United States Patent [19]

Maekawa et al.

[11] Patent Number: 5,702,686
[45] Date of Patent: Dec. 30, 1997

[54] CLEAR DENTRIFICE GEL FOR INTERDENTAL BRUSHES

[75] Inventors: Kiyoshi Maekawa, Mount Prospect; Christina M. Calhoon, Elgin, both of Ill.

[73] Assignee: John O. Butler Company, Chicago, Ill.

[21] Appl. No.: 503,716

[22] Filed: Jul. 18, 1995

[51] Int. Cl.$^6$ .................. A61K 7/16; A61K 7/18
[52] U.S. Cl. .................................. 424/49; 424/52
[58] Field of Search ........................... 424/49–58

[56] References Cited

U.S. PATENT DOCUMENTS

| | | | |
|---|---|---|---|
| 3,337,412 | 8/1967 | Elbreder . | |
| 3,538,230 | 11/1970 | Pader et al. | 424/50 |
| 3,689,637 | 9/1972 | Pader | 424/52 |
| 3,934,000 | 1/1976 | Barth | 424/49 |
| 4,108,978 | 8/1978 | Mazzanobile et al. | 424/49 |
| 4,143,126 | 3/1979 | Gaffar . | |
| 4,254,101 | 3/1981 | Denny | 424/52 |
| 4,267,167 | 5/1981 | Weitzman et al. . | |
| 4,294,894 | 10/1981 | Vellucci . | |
| 4,314,990 | 2/1982 | Denny et al. | 424/52 |
| 4,340,583 | 7/1982 | Wason | 424/52 |
| 4,364,927 | 12/1982 | Sipos et al. . | |
| 4,411,889 | 10/1983 | Caslavsky et al. . | |
| 4,435,380 | 3/1984 | Pader | 424/49 |
| 4,454,110 | 6/1984 | Caslavsky et al. . | |
| 4,485,089 | 11/1984 | Leipold | 424/49 |
| 4,540,576 | 9/1985 | Zahradnik . | |
| 4,584,189 | 4/1986 | Leipold | 424/54 |
| 4,684,517 | 8/1987 | Clipper et al. . | |
| 4,849,212 | 7/1989 | Glandorf et al. . | |
| 4,942,034 | 7/1990 | Hill et al. . | |
| 4,943,429 | 7/1990 | Winston et al. . | |
| 5,051,401 | 9/1991 | Sikes . | |
| 5,071,638 | 12/1991 | Yoshie et al. | 424/49 |
| 5,165,913 | 11/1992 | Hill et al. . | |
| 5,192,529 | 3/1993 | Garlick et al. | 424/49 |
| 5,256,402 | 10/1993 | Prencipe et al. . | |
| 5,275,803 | 1/1994 | Dawson . | |
| 5,279,815 | 1/1994 | Wason et al. . | |
| 5,283,924 | 2/1994 | Kaminski et al. | 15/244.1 |

*Primary Examiner*—Shep K. Rose
*Attorney, Agent, or Firm*—Laff, Whitesel, Conte & Saret, LTD.

[57] ABSTRACT

A clear, mildly abrasive, low-viscosity dentrifice gel for use with twisted wire interdental brushes which comprises optimal humectant, silica abrasive and water concentration levels.

18 Claims, No Drawings

5,702,686

CLEAR DENTRIFICE GEL FOR INTERDENTAL BRUSHES

FIELD OF THE INVENTION

This invention relates generally to dentrifice gels and, more particularly, to a clear, mildly abrasive, low-viscosity dentrifice gel for use with twisted wire interdental brushes.

BACKGROUND OF THE INVENTION

The brushing of teeth serves two important purposes, specifically removing plaque from the teeth and massaging the mouth tissue. This massaging allows the gum to develop a thicker and healthier surface layer for resisting attack from both disease and mechanical abrasion. Unfortunately, conventional toothbrushes are limited in their use to the tooth and gum surfaces that they can reach. For example, the interdental spaces located between and around the teeth, as well as the gum line are difficult to clean with conventional toothbrushes. Therefore, conventional toothbrushes may not effectively remove plaque, stimulate the gums and brush the gum line.

Interdental twisted wire brushes are commonly used to achieve this brushing and massaging because the twisted wire brushes are able to fit within and through the interdental spaces. Unfortunately, conventional toothpastes do not work well with interdental brushes. Given the small size of interdental brushes, applying toothpaste on the brush bristles is very difficult. However, even if toothpaste could be applied on the bristles, it would invariably fall off as the bristles are inserted through the interdental spaces. Thus, a dentrifice gel which sinks into the brush bristles should be used with interdental brushes so that both the bristles and the gel can fit in the interdental spaces.

A dentrifice gel for use with twisted wire interdental brushes should have a low viscosity so that it will sink into the brush bristles. This can be achieved by having a high humectant concentration in the gel. A low viscosity will also enhance the dispersion of the gel around the teeth and gum tissue for more effective cleaning. The dentrifice gel should additionally be only mildly abrasive so as to prevent any damage to the tooth enamel or dentin. It would also be desirable to have a dentrifice gel that can be safely swallowed and is aesthetically pleasing.

There are several prior art references which disclose toothpaste and dentrifice gel compositions. However, none of the references teach using these compositions with twisted wire interdental brushes. In addition, the prior art toothpastes and gels are too viscous and abrasive to be used with interdental brushes.

For example, U.S. Pat. No. 4,314,990 (Denny Jr. et al.) discloses a toothpaste composition comprising a humectant, a silica abrasive, sodium fluoride, a buffering agent and water. The humectant comprises from about 30% to 70% and the silica abrasive comprises from about 6% to 45% by weight of the composition.

U.S. Pat. No. 4,340,583 (Wason) and U.S. Pat. No. 5,279,815 (Wason et al.) disclose a toothpaste composition comprising a humectant, a silica abrasive, a source of fluoride ions, a binding agent and water. The humectant comprises from about 5% to 55% and the silica abrasive comprises from about 6% to 35% by weight of the composition.

U.S. Pat. No. 4,943,429 (Winston et al.) discloses a translucent dentrifice gel comprising sodium bicarbonate, a humectant and water. The sodium bicarbonate comprises from about 5% to 60% and the humectant comprises from about 15% to 60% by weight of the gel. The dentrifice gel may further comprise up to 20% by weight of a secondary abrasive.

SUMMARY OF THE INVENTION

The present invention comprises a dentrifice gel containing from about 70% to 85% by weight of a humectant, not more than about 15% by weight of a silica dental abrasive and not more than about 15% by weight of water.

The resulting clear, mildly abrasive, low-viscosity dentrifice gel sinks into the bristles of an interdental brush, enhances dispersion, and does not damage tooth enamel or dentin. Because the gel is made of food grade materials, it can be safely swallowed.

DETAILED DESCRIPTION OF THE INVENTION

The present invention is directed to a dentrifice gel for use with twisted wire interdental brushes. The dentrifice gel comprises optimal humectant, silica dental abrasive and water concentrations. The optimal concentration levels of these components yield a gel which is clear, mildly abrasive and has a low viscosity. The dentrifice gel also comprises a source of fluoride ions, a buffering agent and a binder, as well as various other preferred optional ingredients as described below.

The humectant should be present in the dentrifice gel in the range of about 70 to 85% by weight of the gel, and preferably in the range of about 80 to 85% by weight. The humectants which may be used in accordance with the invention include sorbitol, glycerine, xylitol and propylene glycol. If sorbitol is employed, a 70% aqueous solution is preferred. A preferred humectant component of the dentrifice gel is a mixture of 70% sorbitol and glycerine, and various ratios may be utilized.

The higher the concentration of the humectant in the dentrifice gel, the lower the viscosity will be. It is preferred that the viscosity of the gel be below 30,000 centipoises (cps). A low viscosity allows the dentrifice gel to sink into the bristles of a twisted wire interdental brush so that both the gel and the bristles can fit in between the teeth. A low viscosity also enhances the dispersion of the gel around the teeth and gums for more effective cleaning.

The silica dental abrasive should be present in the dentrifice gel in the range of about 5 to 15% by weight of the gel, and preferably in the range of about 5 to 10% by weight. The silica abrasive used in the present invention preferably has an average particle size of less than 10 microns and can be obtained from various companies including, but not limited to, Degussa, Crossfield, W. R. Grace, and J. M. Huber Corporation. Precipitated amorphous silica marketed by the J. M. Huber Corporation and known as Zeodent® and Zeofree® are preferred.

A relatively low level of silica abrasive in the dentrifice gel is more gentle on gum tissue and prevents damage to tooth enamel or dentin. This is important in the present invention because interdental brushes, to which the gel will be applied, are often used by people with receding gum lines. Thus, a mildly abrasive gel will be less likely to irritate sensitive gum tissue located between and around the teeth, as well as exposed dentin.

Water should be present in the dentrifice gel in the range of about 5 to 15% by weight of the gel, and preferably, in the range of about 5 to 10%. The water used in the preparation of the dentrifice gel should be purified.

It has been found that the humectant, silica abrasive and water concentration levels control the clarity of the gel. Thus, an optimal balance of the concentration levels of these three components will yield a clearer dentrifice gel. In accordance with the present invention, these optimal levels are about 81% by weight of the humectant, about 9% by weight of the silica abrasive and about 7% by weight of water.

In addition to these three components and corresponding concentration levels which achieve the advantages of this embodiment of the invention, the dentrifice gel also comprises a source of fluoride ions to protect teeth from decay, a buffering agent to maintain the pH and a binder to achieve the desired consistency.

Fluoride ion sources from the group comprising sodium fluoride, potassium fluoride, ammonium fluoride, stannous fluoride and sodium monofluorophosphate may be used in accordance with the invention. Sodium fluoride is preferred. The fluoride should be present in the range of about 0.02 to 0.5% by weight of the dentrifice gel, and preferably in the range of about 0.05 to 0.15%.

The buffering agents which may be used in the dentrifice gel of the present invention are phosphate salts, and preferably orthophosphate salts. Trisodium phosphate is preferred. To achieve the desired buffer capacity, the trisodium phosphate should be present in the range of about 0.05 to 0.25% by weight of the dentrifice gel, and preferably in the range of about 0.07 to 0.13%.

Conventional binders which are employed in the toothpaste art and may be used in the dentrifice gel include gums, derivatives of cellulose and seaweed colloids. Xanthan gum is preferred. The xanthan gum should be present in the range of about 0.1 to 2.0% by weight of the dentrifice gel, and preferably in the range of about 0.1 to 0.5%.

The dentrifice gels of the present invention may also optionally contain a variety of other ingredients typically found in toothpaste compositions. These optional ingredients include emulsifiers, flavoring agents, preservatives, sweeteners and coloring agents.

The emulsifiers which can be used herein can be broadly defined as nonionic surface-active agents, such as polyoxyethylene derivatives of fatty-acid partial esters of sorbitol anhydrides known as Tween® and Polysorbate® surfactants, or combinations thereof. Polysorbate 20 is preferred. Polysorbate 20 should be present in the range of about 0.2 to 5.0% by weight of the dentrifice gel, and preferably in the range of about 0.5 to 2.0%.

Flavoring agents and sweeteners can also be added to the dentrifice gel. Flavoring agents which may be used include, but are not limited to, the mint flavors and their components, and various natural and artificial fruit and plant extracts. The flavoring agent is present in the gel in an amount within the range of about 0.1 to 3.0% by weight. Suitable sweeteners include sodium saccharin, sucrose, lactose, maltose, sorbitol, D-tryptophan, aspartame, xylitol or other sweeteners known to those skilled in the art. These sweeteners may be used alone, or in any mixture thereof, in an amount of about 0.1 to 15% by weight.

The dentrifice gels disclosed herein may optionally contain a preservative. Suitable preservatives include esters of parahydroxybenzoic acid, and would include, but is not limited to methyl, propyl and butyl paraben. The preservative should comprise from about 0.01 to 0.5% by weight of the gel.

Coloring agents may be used to enhance the appearance of the dentrifice gel. Coloring agents such as FD&C Blue No. 1 and Yellow No. 10 may be used in the practice of the present invention in the range of about 0.0005 to 0.01% by weight of the gel.

A further optional ingredient may be added to the dentrifice gel to desensitize teeth. Suitable ingredients for the relief of tooth sensitivities include potassium nitrate, glycerine, strontium chloride, dicalcium phosphate, sodium fluoride, sodium citrate, calcium hydroxide, potassium oxalate, stannous fluoride, or other ingredients known to those skilled in the art. Potassium nitrate is preferred. Potassium nitrate should comprise from about 4.5 to 5.5% by weight of the gel. When potassium nitrate is present in the dentrifice gel, a small amount of basic solution, such as sodium hydroxide, may also need to be added to adjust the pH.

It should be noted that the dentrifice gel of the present invention does not contain any anionic surfactants, such as sodium lauryl sulfate, which is a common ingredient in most conventional toothpastes. Rather, the dentrifice gel comprises only food grade materials, so that it can be applied to teeth and swallowed. The dentrifice gel may be prepared by combining the essential and optional ingredients in any manner known to those skilled in the art. The resulting gel will have a neutral pH in the range of about 6.5 to 7.5.

EXAMPLES

The following examples are intended to be illustrative of the present invention and to teach one of ordinary skill how to make and use the invention. These examples are not intended to limit the invention or its protection in any way.

Example 1

A dentrifice gel in accordance with the present invention was prepared by mixing together the following ingredients:

| Ingredient | Percent by Weight |
|---|---|
| Sorbitol (70% solution) | 69.30 |
| Glycerin | 12.00 |
| Hydrated silica | 9.00 |
| Polysorbate 20 | 1.00 |
| Mint flavor | 0.80 |
| Methyl paraben | 0.20 |
| Sodium fluoride | 0.20 |
| Sodium saccharin | 0.20 |
| Xanthan gum | 0.20 |
| Trisodium phosphate | 0.10 |
| Yellow #10 | 0.0031 |
| Blue #1 | 0.0014 |
| Purified water | Balance |

Example 2

Another dentrifice gel was prepared in accordance with the present invention by mixing together the following ingredients:

| Ingredient | Percent by Weight |
|---|---|
| Sorbitol (70% solution) | 63.33 |
| Glycerin | 12.00 |
| Hydrated silica | 9.00 |
| Potassium nitrate | 5.00 |
| Polysorbate 20 | 2.00 |

-continued

| Ingredient | Percent by Weight |
| --- | --- |
| Mint flavor | 1.00 |
| Xanthan gum | 0.30 |
| Sodium fluoride | 0.24 |
| Sodium saccharin | 0.12 |
| Trisodium phosphate | 0.10 |
| Sodium hydroxide | 0.02 |
| Blue #1 | 0.0008 |
| Purified water | Balance |

While the present invention is described above in connection with preferred or illustrative embodiments, these embodiments are not intended to be exhaustive or limiting of the invention. Rather, the invention is intended to cover all alternatives, modifications, and equivalents included within its spirit and scope, as defined by the appended claims.

What is claimed is:

1. A clear, mildly abrasive, low-viscosity dentrifice gel which can be safely swallowed for use with a twisted wire interdental brush comprising:
   a) from about 70% to about 85% of a humectant;
   b) from about 5% to about 15% of a silica dental abrasive having an average particle size of less than about 10 microns;
   c) from about 5% to about 15% of water; and
   d) from about 0.2% to about 5.0% of an emulsifier.

2. The dentrifice gel of claim 1 wherein the amount of humectant is from about 80% to about 85%.

3. The dentrifice gel of claim 1 wherein the amount of silica dental abrasive is from about 5% to about 10%.

4. The dentrifice gel of claim 1 wherein the amount of water is from about 5% to about 10%.

5. The dentrifice gel of claim 1 further comprising:
   a) from about 0.02% to about 0.5% of a source of fluoride ions;
   b) from about 0.05% to about 0.25% of a buffering agent; and
   c) from about 0.1% to about 2.0% of a binder.

6. The dentrifice gel of claim 5 further comprising from about 0.1% to about 3.0% of a flavoring agent.

7. The dentrifice gel of claim 5 further comprising from about 0.01% to about 0.5% of a preservative.

8. The dentrifice gel of claim 5 further comprising from about 0.1% to about 15% of a sweetener.

9. The dentrifice gel of claim 5 further comprising from about 0.0005% to about 0.01% of a coloring agent.

10. The dentrifice gel of claim 5 further comprising from about 4.5% to about 5.5% of an ingredient to desensitize teeth.

11. The dentrifice gel of claim 1 wherein the humectant is a mixture of sorbitol and glycerine.

12. The dentrifice gel of claim 11 wherein the ingredient to desensitize teeth is potassium nitrate.

13. The dentrifice gel of claim 1 wherein the pH is in the range of about 6.5 to about 7.5.

14. The dentrifice gel of claim 1 wherein the viscosity is not more than 30,000 centipoises to allow the gel to sink into the interdental brush bristles.

15. A clear, mildly abrasive, low-viscosity dentrifice gel which can be safely swallowed for use with a twisted wire interdental brush comprising:
   a) from about 70% to about 85% of a humectant;
   b) from about 5% to about 15% of a silica dental abrasive having an average particle size of less than about 10 microns;
   c) from about 5% to about 15% of water;
   d) from about 0.2% to about 5.0% of an emulsifier; and
   e) from about 0.05% to about 0.25% of a buffering agent to maintain the pH of the dentrifice gel in the range of about 6.5 to 7.5, said dentrifice gel having a low viscosity of less than 30,000 centipoises to allow the gel to sink into the interdental brush bristles.

16. The dentifrice gel of claim 15 further comprising:
   a) from about 0.02% to about 0.5% of a source of fluoride ions;
   b) from about 0.1% to about 2.0% of a binder;
   c) from about 0.1% to about 3.0% of a flavoring agent;
   d) from about 0.01% to about 0.5% of a preservative;
   e) from about 0.1% to about 15% of a sweetener;
   f) from about 0.0005% to about 0.01% of a coloring agent; and
   g) from about 4.5% to about 5.5% of an ingredient to desensitize teeth.

17. The dentrifice gel of claim 15 wherein the humectant is a mixture of sorbitol and glycerine.

18. The dentrifice gel of claim 16 wherein the ingredient to desensitize teeth is potassium nitrate.

* * * * *